United States Patent [19]

November

[11] 4,194,385
[45] Mar. 25, 1980

[54] DENSITOMETER CALIBRATION METHOD

[75] Inventor: Milton H. November, Hacienda Heights, Calif.

[73] Assignee: International Telephone and Telegraph Corporation, New York, N.Y.

[21] Appl. No.: 4,179

[22] Filed: Jan. 17, 1979

[51] Int. Cl.² .............................................. G01N 9/00
[52] U.S. Cl. ........................................ 73/1 R; 73/30; 73/32 A
[58] Field of Search .................... 73/1 R, 32 R, 32 A, 73/30

[56] References Cited

U.S. PATENT DOCUMENTS 3,713,324  1/1973  Miller .................................... 73/1 R

*Primary Examiner*—S. Clement Swisher
*Attorney, Agent, or Firm*—A. Donald Stolzy

[57] ABSTRACT

A method of calibrating a densitometer to meter two gases of different molecular structures by empirically deriving a hole size function of the indicated error for one gas in the density equation of the other and performing tailored reboring of the hole in a production unit in accordance with the hole size derived from the function by determining the full scale error thereof.

5 Claims, 8 Drawing Figures

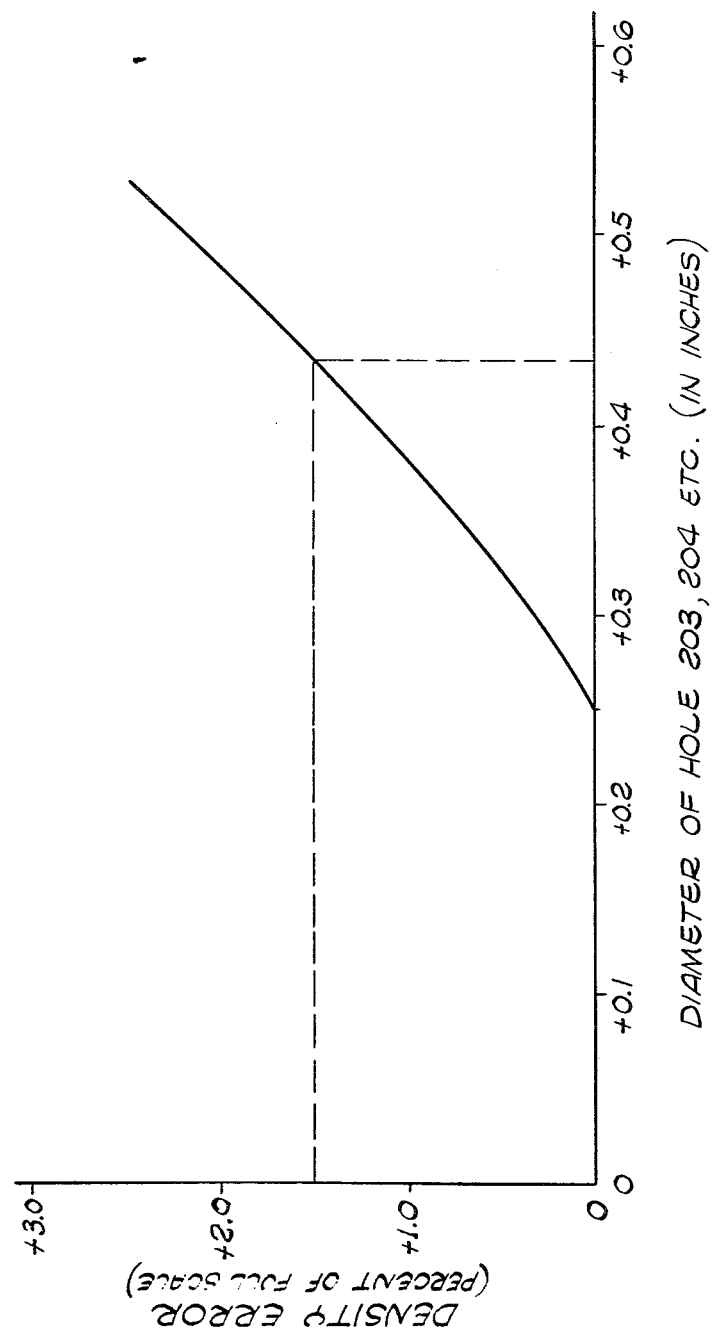

DENSITOMETER CALIBRATION METHOD

BACKGROUND OF THE INVENTION

This invention relates to densitometers, and more particularly to a method of calibrating a vibration densitometer operable to provide a density signal more accurate for two gases of two different molecular structures.

SUMMARY OF THE INVENTION

In accordance with the method of the present invention, the above-described and other disadvantages of the prior art are overcome by determining a hole diameter as a function of error for a vibration densitometer, and tailoring a production unit hole by reboring the hole thereof in accordance with the diameter indicated by the function at the determined density error of the production unit to reduce said error toward zero.

BRIEF DESCRIPTION OF THE DRAWINGS

In the accompanying drawings which illustrate exemplary embodiments of the present invention:

FIG. 8 is a graph of density error plotted as a function of hole diameter desired.

DESCRIPTION OF THE PREFERRED EMBODIMENT

Figure 1:
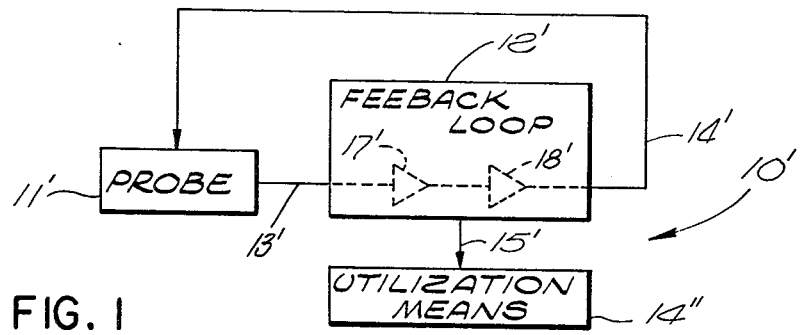
FIG. 1 is a block diagram of a conventional densitometer.

In FIG. 1, a vibration densitometer 10' is shown including a probe 11', a feedback loop 12' connected from and to probe 11' via leads 13' and 14', respectively, and utilization means 14" connected from another output 15' of loop 12'. Densitometer 10' may be identical, if desired, to that disclosed in U.S. Pat. No. 3,677,067, issued July 18, 1972. Attention is also invited to U.S. Pat. No. 3,741,000, issued June 26, 1973. By this reference hereto, the entire contents of both of these patents are hereby incorporated in their entireties herein hereat.

Figure 2:
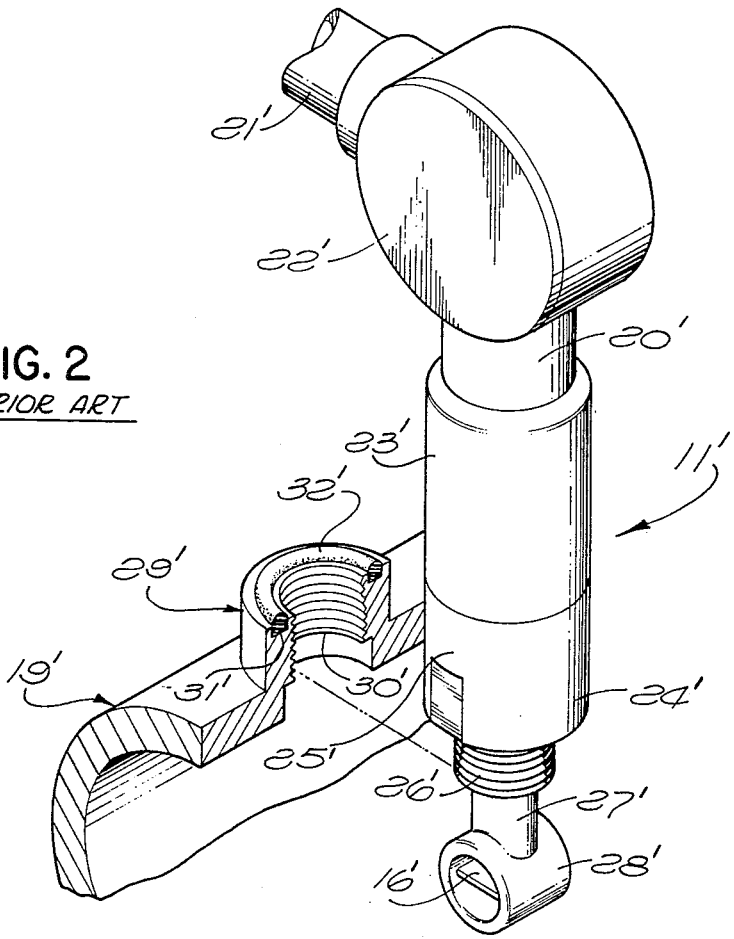
FIG. 2 is a perspective view of a densitometer probe and a pipeline.

Probe 11' contains a vane 16' shown in FIG. 2 which is vibrated. Vane 16' is vibrated because the probe has a piezoelectric crystal pick-up, not shown, the output of which is amplified and the vane 16' vibrated by a magnetostrictive driver, not shown. The resonant vibrational frequency f of vane 16' is a known function of the density of the gas or liquid or other fluid in which the vane 16' is immersed.

If desired, loop 12' in FIG. 1 may have a linearization circuit so that the output signal on lead 15' may have a magnitude directly proportional to density.

Utilization means 14" may be a voltmeter or ammeter calibrated in density, a process controller, a gas flow computer, a net oil computer or otherwise.

In accordance with the foregoing, the word "densitometer" is hereby defined to include or not include utilization means 14". Note will be taken that the densitometer in many cases will be manufactured and sold without any utilization means 14". Such utilization means 14" would be supplied by the customer.

The vibration densitometer 10' is essentially an electromechanical oscillator. The oscillator obviously has losses. Loop 12', therefore, includes at least one amplifier. Two amplifiers 17' and 18' are illustrated in loop 12' in FIG. 1.

Probe 11' is shown again in FIG. 2 for mounting in a pipeline 19'.

Densitometer 10' may, alternatively, be, if desired, identical to that disclosed in said U.S. Pat. No. 3,741,000.

The probe 11' may be identical to the probe shown in the said U.S. Pat. No. 3,741,000 or with certain exceptions.

The probe 11' has conduits 20' and 21', and a pull box 22'. Conduits 20' and 21' and pull box 22' simply serve as enclosures for the output leads from probe 11' to loop 12' shown in FIG. 1.

Conduit 21' is threaded to pull box 22' in a manner not shown. Conduit 20' is threaded to pull box 22' and to a body 23' of probe 11'. Conduits 20' and 21', pull box 22' and body 23' are, thus, all fixed together. A body 24' is fixed to body 23'. Body 24' has an upper portion 25' of a larger diameter and a lower portion 26' of a smaller diameter that is externally threaded. A shank 27' is fixed to threaded portion 26' and to a cylinder 28'. Vane 16' is mounted in a fixed position along its opposite edges to cylinder 28'.

Pipeline 19' has a hollow cylindrical projection 29' permitting probe 11' to be threaded and lowered thereinto, projection 29' having an axis perpendicular to axis of pipeline 19'. Projection 29' is internally threaded at 30'. Probe portion 26' is threaded into projection 29' at the thread 30'. Projection 29' has an O-ring groove 31', and an O-ring 32' therein that seals with a shoulder, not visible in FIG. 2, at the bottom of body 24' where the diameter of the probe is reduced to the diameter of the threaded portion 26' thereof. The bottom surface of the body 24' may be flat and in a plane perpendicular to the vertical axis of the probe 11' so as to rest on O-ring 32', O-ring 32' thereby sealing probe 11' inside pipeline 19'. At least that portion of probe 11' below the thread 26', thus, protrudes downwardly inside pipeline 19' below the inside diameter thereof.

All the structures shown in FIGS. 1 and 2 may be entirely conventional, if desired.

Figure 3:
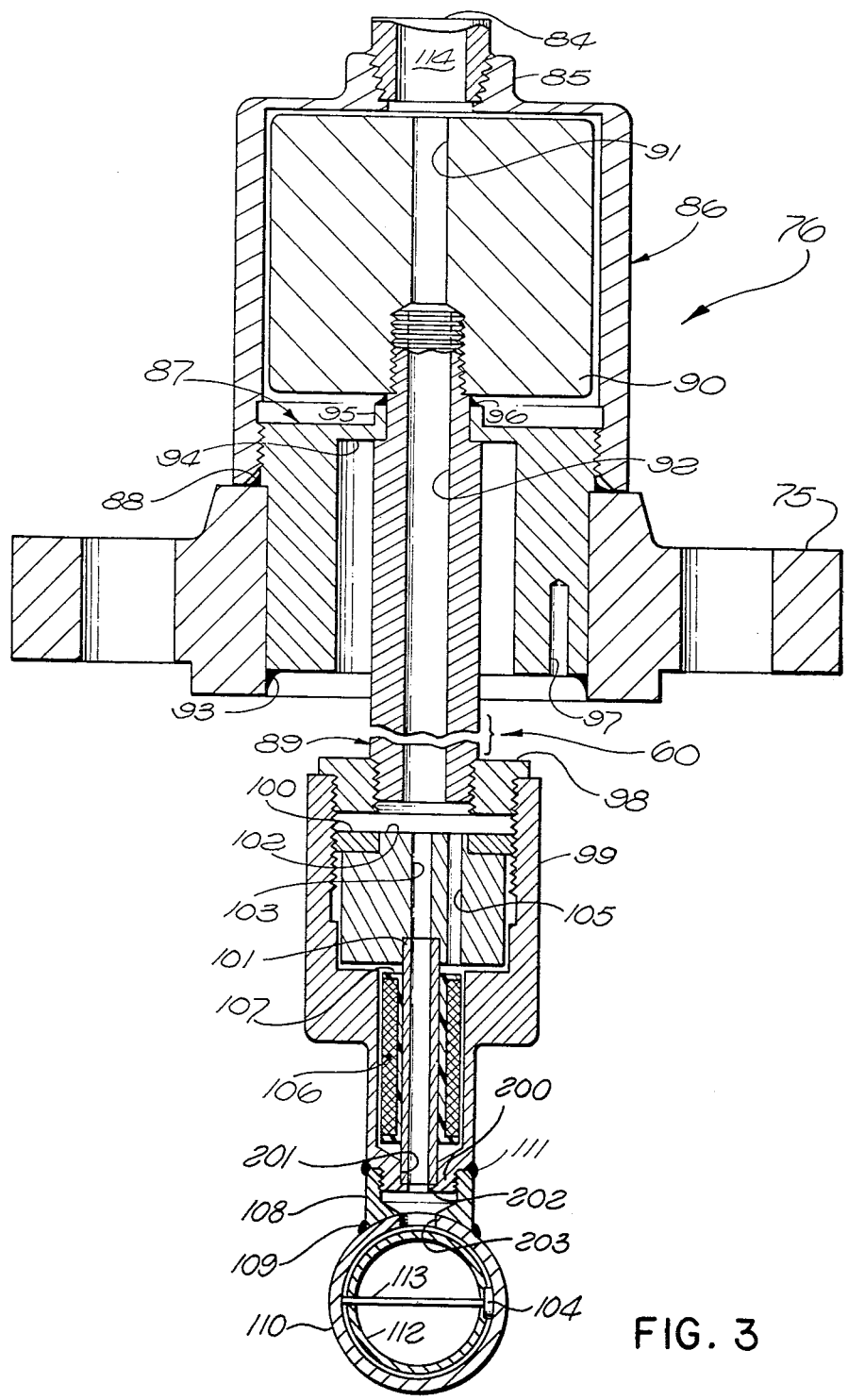
FIG. 3 is a vertical sectional view of a densitometer probe constructed for use in accordance with the present invention.

A vertical sectional view of a probe 60 is shown in FIG. 3 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 and may be welded thereto, if desired. Cylinder 90 is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto and also welded, if desired.

A ring 100 is threaded into body 99. A magnetostrictive tube 101 which is hollow and open at both ends is press fit into a body 102 and press fit into the lower end 200 of body 99. Body 102 is similar to a body disclosed in the said U.S. Pat. No. 3,741,000, and may be identical thereto, if desired. Alternatively, body 102 may have one hole 103 to receive lead wires from a piezoelectric crystal 104, and a hole 105 to receive lead wires from a drive coil 106 wound on a dielectric spool 107 press fit onto tube 101. A ferrule 108 is welded at 109 to a cylinder 110. Body 99 is threaded into ferrule 108 and welded thereto at 111. Tube 101 extends at the bottom thereof, through a circular hold 201 in the end 200 of body 99. End 201 has a shoulder 202 that the lower end of tube 101 abuts.

Cylinder 110 has a circular hole 203 therethrough.

A vane 113 is fixed inside cylinder 110 in a manner identical to that illustrated in the said U.S. Pat. No. 3,677,067. The same is true of crystal 104.

The utility of a vibration densitometer employing the structure disclosed herein is described in detail in the said patents.

Cylinders 110 and 112, vane 113, and crystal 104 may be identical to those disclosed in the last mentioned patent, if desired.

A more detailed explanation of the operation of a vibration densitometer employing the structure disclosed herein is set forth in the said patents.

It is common to use a preamplifier in the probe. Such a preamplifier may be employed at 114 in FIG. 15, or at any other convenient location, as desired.

When probe 60 is used in the system of either one of the said patents, the system may be constructed so that utilization means 14" can be an indicator which will read in pounds per cubic foot, for example.

It is known that density d of a gas in which vane 113 is immersed can be calculated by $$d = AT^2 - B \quad (1)$$

where $$T = 1/f \quad (2)$$

f is the frequency of vibration of vane 113, and A and B are constants selected to curve fit (1) to true density as explained in the said U.S. Pat. No. 3,677,067.

The system will have a small indicated density error when A and B are selected for one gas and the measurement is taken for a different gas. The present invention is then constructed without reboring 203 as at 204 in FIG. 7, or by reboring both hole 204 and a portion of ferrule at 205.

Customers may want to perform their own check of calibration in nitrogen gas and compare the nitrogen constants with those constants provided by the manufacturer for methane to verify the methane constants. A methane check may not be run by the customers so as to make it unnecessary to take safety steps because of the explosive or inflammable character of methane.

The present invention has been reduced to practice and it works. The theory of operation is not obvious and only a modest explanation thereof can be given.

Figures 4, 5:
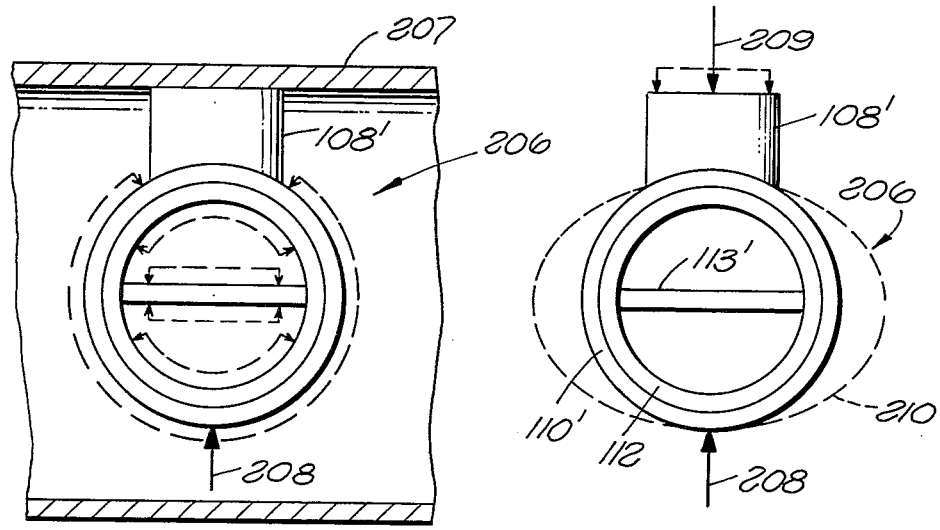
FIGS. 4 and 5 are diagrammatic views of probe end portions illustrating the effects of pressure thereon.

In FIG. 4, for purposes of explanation only, a ferrule 108' is fixed to an assembly 206 identical to that inside and including cylinder 110 (FIG. 3), and to a pipeline 207. The sum of the forces on assembly 206 may be represented by a resultant force 208. If desired, ferrule 108' may be identical to ferrule 108 (FIG. 3). Pipeline 207 thus applies a resultant force 209 equal to force 208. See FIG. 5. Ferrule 108' acts as a stiffener for assembly 206. Force 208 thus tends to make assembly 206 somewhat elliptical as indicated at 210. This reduces or changes the compression of vane 113' and causes an error because the resonant vibrational frequency of vane 113' is a function of its tension or compression.

Commonly cylinders 110' and 112' have an interference fit and vane 113' remains in compression from zero to full scale with a gas in pipeline 207.

The method of the present invention overcomes the 210 problem although a further explanation therefor may be difficult.

A disconcerting effect of changes in pipeline pressure is that the van der Waal's equation is not absolutely accurate for different gases. The resonant vibrational frequency of vanes 113 and 113' can thus be different for different gases because of their different gas constants and different sonic velocities.

Figures 6, 7:
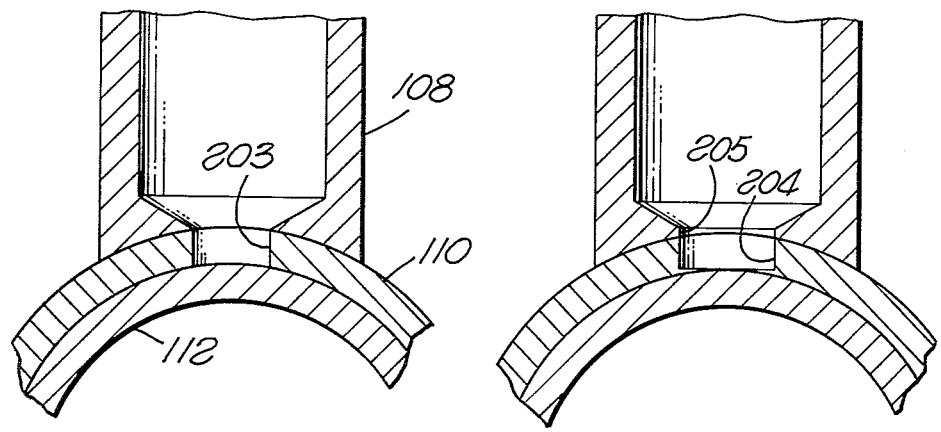
FIG. 6 is an enlarged vertical sectional view of a portion of the probe shown in FIG. 3.
FIG. 7 is a view similar to FIG. 6 with a probe hole rebored.

The method of the present invention starts with a production unit as shown, for example, in FIG. 6, and reboring hole 203 as at 204 and 205 in FIG. 7 from information derived from a curve, for example, like a curve 211 shown in FIG. 8.

The curve of FIG. 8 can be obtained empirically as follows. Utilize a conventional system of the type described where the input signal to means 14" (FIG. 1) is computed by loop 12' thus:

$$d = AT^2 - B \quad (3)$$

(1) Use an experimental probe 60 of the type shown in FIG. 3 (it may be a production unit) and find A and B for nitrogen, for example, in the conventional way. The experimental probe may have a hole 203 (FIG. 6) of a diameter s.

(2) Place the probe in methane, for example, at about full scale pressure (e.g., 5 pounds per square inch).

(3) Determine the period $T = T_{ca}$ and then apparent density $d_{ca}$ thus $$d_{ca} = AT_{ca}^2 - B \quad (4)$$

where A and B in equation (4) are the same as those found in step (1) for nitrogen. Start with a diameter of hole 203 equal to, for example, 0.25 inch (see FIG. 8).

(4) Determine the true density $d_t$ of the methane from measured pressure P and temperature t as, for example, $$d_t = P/R_t$$

where R is the gas constant of methane.

(5) Compute $$[100] \left[ \frac{d_t - d_{ca}}{d_t} \right] \quad (5)$$

for the 0.25 inch hole 203.

(6) Rebore hole 203 and make it larger one or more times in successive increments.

(7) For each successive increment, again perform all the steps (1) through (5) and plot term (5) as a function of the diameter of the hole at each successive increment to form curve 211. In step (1), for each increment, note that A and/or B may or may not change.

Some production units need not be tailored. However, when that is desired, $$y = [100] \left[ \frac{d_t - d_{ca}}{d_t} \right] \quad (6)$$

is computed for those that are in the form of FIG. 6. If $y = -1.5$ percent, for example (FIG. 8, line 212), the desired reboring diameter of hole 203 can be found at 213 (e.g., 0.435 inch).

y is usually negative. Thus the $+1.5$ percent at 212 in FIG. 8 tends to cancel out the error of equation (3) when curve fitted to nitrogen and applied to methane.

After reboring, A and B for both nitrogen and methane are conventionally determined and supplied to the customer. y at full scale is then not normally $-0.6$ percent $> y > +0.6$ percent.

What is claimed is:

1. The method of calibrating a densitometer, said method comprising the steps of: providing an experimental probe having contacting concentric inner and outer cylinders fixed relative to each other, said outer cylinder having a hole therethrough, said hole having an axis and a diameter s, said experimental probe including a mounting ferrule fixed to stiffening said outer cylinder around said hole; said experimental probe also including a vane fixed in a diametrical position relative to said inner and outer cylinders inside thereof and normal to said hole axis; providing first driver means to vibrate said vane at a frequency f such that the density d of a first known fluid in which said probe is immersed can be calculated by the formula $$d = AT^2 - B$$

where $$T = 1/f$$

A is a constant
B is a constant,

A and B being selected to curve fit d to true density; immersing said experimental probe in a second known fluid at the same said full scale and measuring $T = T_{ca}$ thereat; determining the apparent density $d_{ca}$ of said second fluid by the formula $$d_{ca} = AT_{ca}^2 - B;$$

empirically deriving a predetermined function $$s = [f] \left[ \frac{d_t - d_{ca}}{d_t} \right]$$

deriving $d_{ca}$ by changing hole size s,
where $d_{ca}$ is variable with s, s is the diameter of said hole, and $d_t$ is the full scale true density; providing a production probe and driver means of the type aforesaid, said production probe having an outer cylinder hole; determining the equivalent $d_{cb}$ of $d_{ca}$ for one production probe hole size; enlarging said production probe hole to a size indicated by utilizing $d_{cb}$ in said predetermined function to find a corresponding value of s.

2. The invention as defined in claim 1, wherein said first fluid is nitrogen gas, and said second fluid is methane gas.

3. The invention as defined in claim 2, wherein both of said probes, before rebored, have ferrules flush around said hole, said production probe ferrule being enlarged to the same diameter as said production probe hole on reboring.

4. The invention as defined in claim 1, wherein both of said probes, before rebored, have ferrules flush around said hole, said production probe ferrule being enlarged to the same diameter as said production probe hole on reboring.

5. The method of calibrating a densitometer, said method comprising the steps of: determining a hole diameter of a vibration densitometer probe; determining the hole size function of density error of a vibration densitometer; and tailoring a production unit hole by reboring the hole thereof in accordance with the diameter indicated by the said function at the determined density error of the production unit to reduce said error toward zero.

* * * * *